United States Patent
Ugurbil et al.

(10) Patent No.: US 9,689,948 B2
(45) Date of Patent: Jun. 27, 2017

(54) SYSTEM AND METHOD FOR REDUCING RADIO FREQUENCY PEAK VOLTAGE AND POWER REQUIREMENTS IN MAGNETIC RESONANCE IMAGING USING TIME-SHIFTED MULTIBAND RADIO FREQUENCY PULSES

(71) Applicant: REGENTS OF THE UNIVERSITY OF MINNESOTA, St. Paul, MN (US)

(72) Inventors: Kamil Ugurbil, Minneapolis, MN (US); Edward Auerbach, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 608 days.

(21) Appl. No.: 14/349,195

(22) PCT Filed: Oct. 3, 2012

(86) PCT No.: PCT/US2012/058541
§ 371 (c)(1),
(2) Date: Apr. 2, 2014

(87) PCT Pub. No.: WO2013/052535
PCT Pub. Date: Apr. 11, 2013

(65) Prior Publication Data
US 2014/0253120 A1 Sep. 11, 2014

Related U.S. Application Data

(60) Provisional application No. 61/542,585, filed on Oct. 3, 2011.

(51) Int. Cl.
G01R 33/561 (2006.01)
A61B 5/055 (2006.01)
G01R 33/483 (2006.01)

(52) U.S. Cl.
CPC .......... G01R 33/5615 (2013.01); A61B 5/055 (2013.01); G01R 33/4835 (2013.01)

(58) Field of Classification Search
CPC .. G01R 33/5615; G01R 33/4835; A61B 5/055
See application file for complete search history.

(56) References Cited

U.S. PATENT DOCUMENTS 5,422,572 A 6/1995 Yao
6,806,706 B2 10/2004 Gurr
(Continued)

OTHER PUBLICATIONS

The International Search Report and Written Opinion as mailed on Dec. 11, 2012 for International Application No. PCT/US2012/058541.

(Continued)

*Primary Examiner* — Gregory H Curran
(74) *Attorney, Agent, or Firm* — Quarles & Brady LLP

(57) ABSTRACT

A system and method for producing images depicting a plurality of slice locations in a subject using a magnetic resonance imaging ("MRI"} system is provided. In particular, the system and method utilize time-shifted multiband radio frequency ("RF"} pulses to lower peak voltage and peak power requirements when using conventional multiband RF pulses. A time-shifted multiband RF pulse includes at least two component RF pulses, which may be single-band or multiband pulses. The component RF pulses are designed such that they do not have temporal footprints that completely overlap; although, they may have temporal footprints that partially overlap or do not overlap at all. The MRI system is used to acquire magnetic resonance signals formed in response to a time-shifted multiband RF pulse and, from these acquired signals, images depicting each of the plurality of slice locations in the subject are reconstructed.

24 Claims, 11 Drawing Sheets

(56) References Cited

U.S. PATENT DOCUMENTS

| | | |
|---|---|---|
| 9,474,454 B2 * | 10/2016 | Feinberg .............. A61B 5/0263 |
| 2009/0278538 A1 | 11/2009 | Chen et al. |
| 2010/0085046 A1 | 4/2010 | Larson et al. |
| 2011/0087090 A1 * | 4/2011 | Boernert ................ A61B 5/055 600/411 |
| 2011/0144474 A1 | 6/2011 | Ouwerkerk |

OTHER PUBLICATIONS

Gadi Goelman, et al., "Chemical-Shift Artifact Reduction in Hadamard-Encoded MR Spectroscopic Imaging at High (3T and 7T) Magnetic Fields," Magnetic Resonance in Medicine 58, 2007, pp. 167-173, Wiley-Liss, Inc.

Gadi Goelman, "Two Methods for Peak RF Power Minimization of Multiple Inversion-Band Pulses," MRM 37, 1997, p. 658-665, Williams & Wilkins.

Ching Yao, et al., "Parallel Multi-Slice Imaging with Limited Peak RF Power," Toshiba America MRI, Inc., South San Francisco, CA.

* cited by examiner

SYSTEM AND METHOD FOR REDUCING RADIO FREQUENCY PEAK VOLTAGE AND POWER REQUIREMENTS IN MAGNETIC RESONANCE IMAGING USING TIME-SHIFTED MULTIBAND RADIO FREQUENCY PULSES

CROSS-REFERENCE TO RELATED APPLICATIONS

This application represents the U.S. National Stage of International Application No. PCT/US2012/058541, filed Oct. 3, 2012 which claims the benefit of, and incorporates by reference U.S. Provisional Patent Application Ser. No. 61/542,585, filed on Oct. 3, 2011, and entitled "POWER REDUCTION WITH MULTIBAND PULSES BY TIME SHIFTING INDIVIDUAL RF PULSES OF A MULTI-BAND RF PULSE."

STATEMENT REGARDING FEDERALLY SPONSORED RESEARCH

This invention was made with government support under RR008079, EB015894, and MH091657 awarded by the National Institutes of Health. The government has certain rights in the invention.

BACKGROUND OF THE INVENTION

The field of the invention is systems and methods for magnetic resonance imaging ("MRI"). More particularly, the invention relates to systems and methods for reducing peak power requirement and/or power deposition per pulse during a substantially simultaneous multi-slice acquisition.

Since its initial application, scan time for volume coverage with echo-planar imaging ("EPI") or spiral-type MRI data acquisitions has not substantially decreased. Nearly all the successful efforts to shorten EPI acquisition times have targeted reducing the number of refocused echoes needed for spatial encoding to form an image, such as by means of partial Fourier imaging, parallel imaging, or sparse data sampling techniques. Although these approaches decrease scan time for spatial encoding of a single slice in EPI, they do not necessarily reduce the time required for image acquisitions by a significant amount. This lack in scan time reduction is because if multiple slices are employed to cover the volume—as is most often the case—the time of volume coverage is equal to the product of the number of slices needed to cover the volume and the acquisition period of each slice. The image acquisition period for each slice remains significant even when spatial encoding times are shortened by techniques like parallel imaging. This lack of scan time reduction is especially true when a physiological contrast preparation period (e.g. for imaging neuronal activity or water diffusion) precedes the spatial encoding period for each slice; the former can equal or exceed the latter in rapid imaging sequences such as EPI because it must be repeated for each slice. The problem is the same for fast acquisition techniques such as turbo-spin echo ("TSE") or fast spin echo ("FSE"); namely, multiple refocused echoes are formed using 180-degree pulses, as opposed to gradient reversal in EPI, to cover multiple k-space lines.

The foregoing problem also exists for normal imaging where one k-space line is collected after each radio frequency ("RF") excitation pulse, whether sampling k-space along a radial trajectory or along a rectilinear trajectory, as in a gradient-recalled echo ("GRE") pulse sequence or a spin-echo ("SE") pulse sequence. In fact, the problem is exacerbated in these cases because each slice is collected not in a single application of the RF pulse (as is done in single shot EPI) or in few shots of the RF pulse (as in segmented EPI); rather, the RF pulse is applied for each k-space line, one k-space line at a time, requiring numerous application of the RF pulse to generate a single image.

Recently, significant shortening of the scan time required for volume coverage has been demonstrated by "slice multiplexing," in which multiple image slice locations are excited and acquired simultaneously using a multiband ("MB") radio frequency ("RF") pulse, a technique commonly referred to as multiband imaging.

In MB imaging there are number of limitations. One limitation is the RF power required to produce the multiband RF pulses. This limitation arises because an MB pulse with an MB factor—the number of simultaneously excited slices—greater than one requires substantial increased power relative to when the same pulse form is employed to excite a single slice versus multiple slices.

The RF pulse with an MB factor greater than one can be viewed as the sum of all the individual RF pulses that excite one slice, which results in a pulse that increases the voltage applied to the coil linearly with the number of pulses; the power required for one application of the pulse then goes as the square of the voltage integrated over the pulse duration. Maximal MB factors that can be practically achieved due to power limitations may arise because of the maximum voltage, current, or power available in the MRI system, which may in turn be imposed by the output capacity of RF amplifiers used in the system or the voltage, current, or power tolerance of the RF front end (i.e., the components involved in the delivery of the RF pulse to the RF coil used to transmit RF to the sample being studied), including the RF coil itself. Alternatively, the achievable MB factor, may be limited because of power deposition into the subject. In human imaging, power deposition averaged over a given period of time cannot exceed limits dictated by regulatory agencies such as the FDA.

SAR, which is a measure of the rate at which energy is absorbed by the body when exposed to an RF electromagnetic field and is measured in watts per kilogram of tissue ("W/kg"), is a concern when conducting MRI experiments on human subjects. As noted above, SAR is especially a concern during the simultaneous excitation of multiple slice locations. This is because when multiple RF pulses are simultaneously employed, the local electric fields generated by each RF pulse undergo local superposition and local extremes in electric field magnitude may arise, leading to spikes in local and global SAR that are of concern to regulatory bodies in both the United States and Europe. For a discussion of these regulatory concerns in the United States, see, for example, Center for Devices and Radiologic Health "Guidance for the Submission of Premarket Notifications for Magnetic Resonance Diagnostic Devices," *Rockville, Md.: Food and Drug Administration;* 1998, and in Europe, see, for example, International Electrotechnical Commission, "International Standard, Medical Equipment-Part 2: Particular Requirements for the Safety of Magnetic Resonance Equipment for Medical Diagnosis, 2nd Revision," *Geneva: International Electrotechnical Commission;* 2002.

The need to stay below safe SAR limits often requires unfavorable tradeoffs in acquisition parameters such as reduced bandwidth of the RF pulse, reduced flip angle of the RF pulse, or increased repetition time between consecutive applications of RF pulses needed to complete the acquisition of a single volume-of-interest (i.e., inter-pulse TR) or between consecutive acquisitions of the volume-of-interest when the same volume is to be imaged repeatedly (volume TR). SAR becomes especially problematic at field strengths of 3T and higher, where the power deposited for a given flip angle increases approximately quadratically with magnetic field magnitude; thus, an increase of as much as four-fold as compared to 1.5T applications can be present.

It would therefore be desirable to provide a method manipulating spins at multiple slice locations with a reduction in peak voltage, peak power, and/or power deposition, which may be measured as SAR. Examples of spin manipulation include excitation, inversion, and refocusing. Such a method would broaden the applicability of multiband RF pulses to imaging pulse sequences other than historically low peak RF pulse power and low SAR sequences, and would allow for improving other imaging parameters, such as TR and volume coverage.

SUMMARY OF THE INVENTION

The present invention overcomes the aforementioned drawbacks by providing a system and method for reducing the peak voltage requirement, peak power requirement, and/or power deposition when imaging with multiband RF pulses by employing time-shifted multiband pulses that are composed of individual component RF pulses with temporal footprints that do not completely overlap, as they do in conventional multiband RF pulses.

It is an aspect of the invention to provide a method for producing images depicting a plurality of slice locations in a subject using an MRI system. The method includes directing the MRI system to perform a pulse sequence that includes generating a multiband RF pulse. This multiband RF pulse is generated by generating a first component RF pulse having a center frequency associated with a first slice location, the first component RF pulse being generated at a first time, and by generating a second component RF pulse having a center frequency associated with a second slice location that is different than the first slice location, the second component RF pulse being generated at a second time that is shifted relative to the first time. The MRI system then acquires k-space data from the plurality of slice locations by sampling magnetic resonance signals formed in response to the generated multiband RF pulse. Images depicting each of the plurality of slice locations in the subject are then reconstructed from the acquired k-space data.

It is another aspect of the invention to provide an MRI system that includes a magnet system configured to generate a polarizing magnetic field about at least a portion of a subject arranged in the MRI system, a plurality of gradient coils configured to apply a magnetic gradient field to the polarizing magnetic field, an RF system that includes at least one RF coil configured to apply an RF field to the subject and to receive magnetic resonance signals therefrom, and a computer system. The computer system is programmed to direct the RF system to generate a time-shifted multiband RF pulse that rotates spin magnetization in a plurality of slice locations in the subject, the time-shifted multiband RF pulse being composed of a first component RF pulse having a first center frequency associated with one of the plurality of slice locations and a second component RF pulse having a second center frequency associated with another of the plurality of slice locations, the first component RF pulse and the second component RF pulse having temporal footprints that do not completely overlap. The computer system is also programmed to direct the RF system to receive magnetic resonance signals formed in response to the time-shifted multiband RF pulse, the magnetic resonance signals being received from the plurality of slice locations, and to reconstruct images depicting each of the plurality of slice locations in the subject from the received magnetic resonance signals.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

As will be described below in detail, systems and methods for reducing peak voltage requirement, peak power requirement, and/or power deposition per radio frequency ("RF") pulse are provided. When RF pulses and subsequent image acquisition are repeated to cover a volume, cover multiple consecutive slices, or cover multiple volumes in a time series, power deposition is averaged over a period of time using the power deposited per pulse and the pulse repetition time ("TR"). This averaging takes place over a period of time specified by regulatory agencies, such as the FDA. The power deposition so calculated is generally quantified as the specific absorption rate ("SAR"). The systems and methods of the present invention provide for SAR reduction while keeping the TR and number of simultaneously-excited slices the same during a substantially simultaneous multi-slice acquisition. Alternatively, the systems and methods of the present invention can provide for increased data acquisition speeds while maintaining the same SAR level due to peak power reduction.

Figure 1:
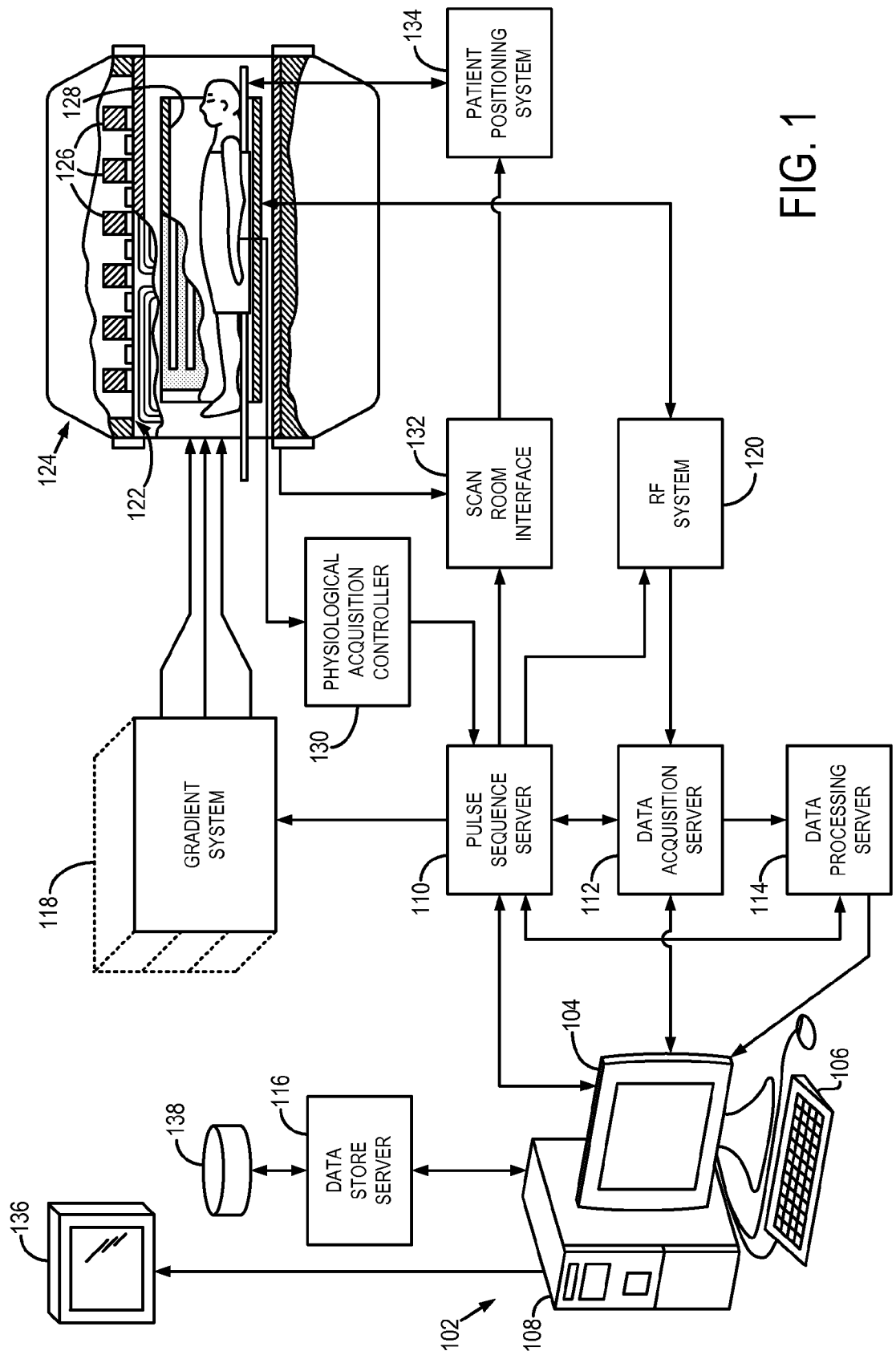
FIG. 1 is a block diagram of an example of a magnetic resonance imaging ("MRI") system.

Referring particularly now to FIG. 1, an example of a magnetic resonance imaging ("MRI") system 100 is illustrated. The MRI system 100 includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system 100. The workstation 102 is coupled to four servers: a pulse sequence server 110; a data acquisition server 112; a data processing server 114; and a data store server 116. The workstation 102 and each server 110, 112, 114, and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF waveforms are applied to the RF coil 128, or a separate local coil (not shown in FIG. 1), by the RF system 120 to perform the prescribed magnetic resonance pulse sequence. Responsive MR signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF preamplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \qquad (1);$$

and the phase of the received MR signal may also be determined:

$$\phi = \tan^{-1}\left(\frac{Q}{I}\right). \qquad (2)$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. By way of example, the data acquisition server 112 acquires MR data and processes it in real-time to produce information that may be used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

Figure 2:
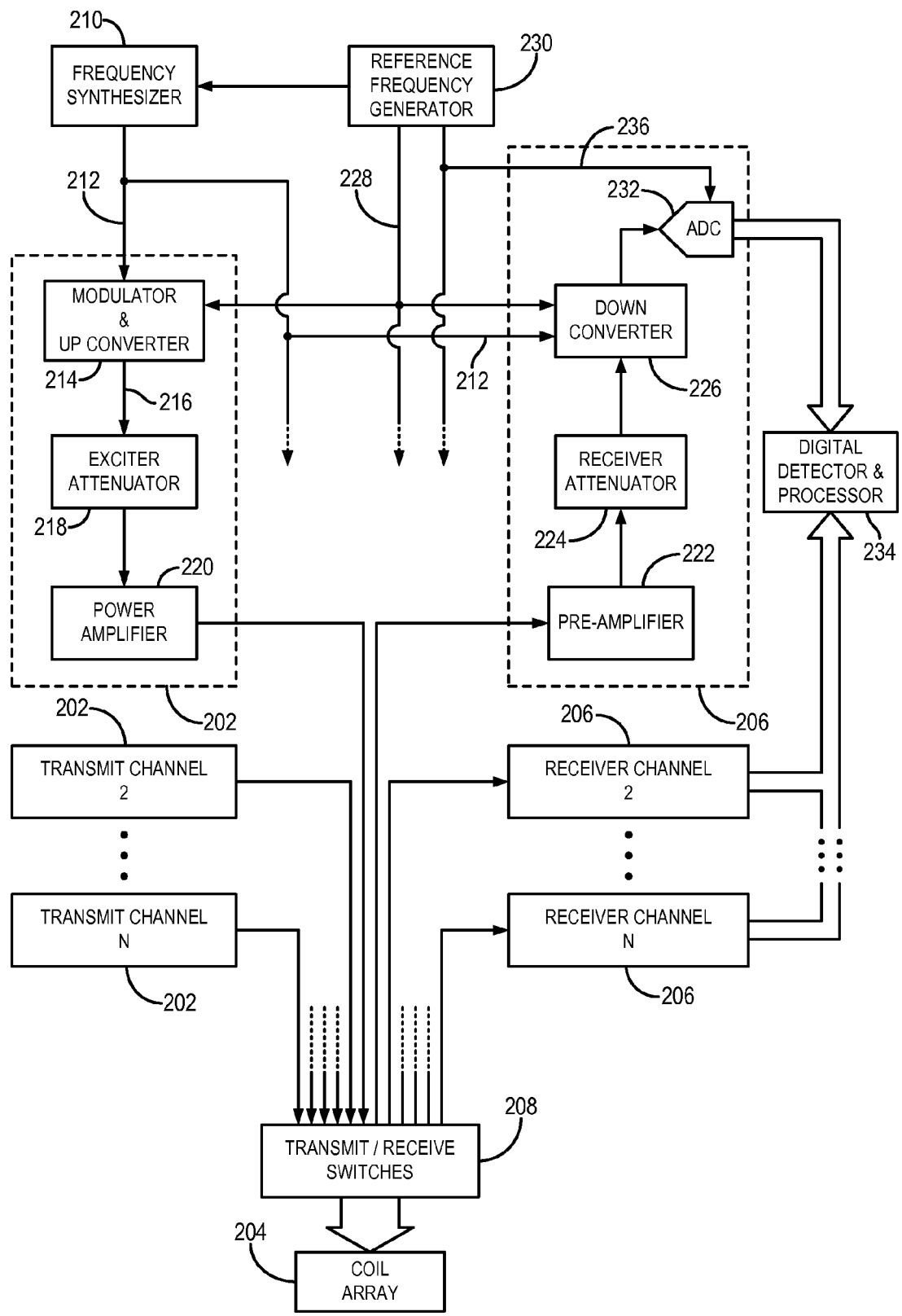
FIG. 2 is a block diagram of an example of a radio frequency ("RF") system that may form part of the MRI system of FIG. 1.

As shown in FIG. 1, the radiofrequency ("RF") system 120 may be connected to the whole body RF coil 128, or, as shown in FIG. 2, a transmission section of the RF system 120 may connect to one or more transmit channels 202 of an RF coil array 204 and a receiver section of the RF system 120 may connect to one or more receiver channels 206 of the RF coil array 204. The transmit channels 202 and the receiver channels 206 are connected to the RF coil array 204 by way of one or more transmit/receive ("T/R") switches 208. The receiver channel 206 may also be an assembly of coils separate from the transmit coil array. In such a configuration, the T/R switches 208 are not needed. The transmit coil elements are detuned or otherwise rendered dysfunctional during the receive operation, and the receiver coil elements are similarly detuned or otherwise rendered dysfunctional during operation of the transmit coils. Such detuning may be accomplished with appropriate control logic signals.

Referring particularly to FIG. 2, the RF system 120 includes one or more transmit channels 202 that produce a prescribed RF electromagnetic field. The base, or carrier, frequency of this RF field is produced under control of a frequency synthesizer 210 that receives a set of digital signals from the pulse sequence server 110. These digital signals indicate the frequency, amplitude, and phase of the RF carrier signal produced at an output 212. The RF carrier is applied to a modulator and, if necessary, an up converter 214 where its amplitude and phase is modulated in response to a signal, R(t), also received from the pulse sequence server 110. The signal, R(t), defines the envelope of the RF pulse to be produced and is produced by sequentially reading out a series of stored digital values. These stored digital values may be changed to enable any desired RF pulse envelope to be produced.

The magnitude of the RF pulse produced at output 216 is attenuated by an attenuator circuit 218 that receives a digital command from the pulse sequence server 110. The phase of the RF pulse may also be altered using phase shifters (not shown). The modulated RF pulses are then applied to a power amplifier 220 that drives one element of the RF coil array 204, or several such elements that are electrically coupled. Multiple transmit channels then drive other elements of the multichannel transmit coil array.

The MR signal produced by the subject is picked up by the RF coil array 202 and applied to the inputs of the set of receiver channels 206. A preamplifier 222 in each receiver channel 206 amplifies the signal, which is then attenuated, if necessary, by a receiver attenuator 224 by an amount determined by a digital attenuation signal received from the pulse sequence server 110. The received signal is at or around the Larmor frequency, and this high frequency signal may be down converted in a two step process by a down converter 226. In an example of such a process, the down converter 226 first mixes the MR signal with the carrier signal on line 212 and then mixes the resulting difference signal with a reference signal on line 228 that is produced by a reference frequency generator 230. The MR signal is applied to the input of an analog-to-digital ("A/D") converter 232 that samples and digitizes the analog signal. As an alternative to down conversion of the high frequency signal, the received analog signal can also be detected directly with an appropriately fast analog-to-digital ("A/D") converter and/or with appropriate undersampling. The sampled and digitized signal may then be applied to a digital detector and signal processor 234 that produces in-phase (I) and quadrature (Q) values corresponding to the received signal. The resulting stream of digitized I and Q values of the received signal are output to the data acquisition server 112. In addition to generating the reference signal on line 228, the reference frequency generator 230 also generates a sampling signal on line 236 that is applied to the A/D converter 232.

As discussed above, a multiband RF pulse may be used to simultaneously rotate the net magnetization of spins in multiple slice locations. The number of slices that are simultaneously affected by a multiband RF pulse is referred to as the multiband factor ("MB factor") of the RF pulse. For simplicity, a multiband RF pulse may be referred to by its MB factor. Thus, a multiband RF pulse that affects four slice locations may be referred to either as a multiband RF pulse having an MB factor of four or, more simply, as an MB4 multiband RF pulse. An RF pulse with an MB factor greater than one can be viewed as an RF pulse composed of the sum of individual component RF pulses, where each component RF pulse affects the spins in one of the multiple slice locations. As a result of their composition, multiband RF pulses require more peak voltage power than a single-band RF pulse. In particular, the peak voltage required to generate a multiband RF pulse increases linearly with the MB factor; thus, the power required to generate the pulse and power deposition caused by this multiband RF pulse increases with the MB factor as the voltage is squared and integrated over pulse duration.

Peak voltage and power requirements may be reduced with appropriately designed multiband RF pulses. Because of these reduced peak voltage and/or peak power, an increased rate of volume coverage, or a larger number of acquired slices, can be achieved. The inventors have discovered that the peak voltage power, peak voltage, and power alone (i.e., without significant alterations in power deposition per unit pulse) may be reduced by partially or fully shifting the component RF pulses, or subgroups of these components, in time. This runs contrary to the conventional multiband RF pulse design, which requires the component RF pulses to be applied all at the same time. Because a multiband RF pulse generated in this manner is composed of a plurality of component RF pulses that are shifted in time relative to each other, the multiband RF pulse is herein referred to as a "time-shifted multiband RF pulse." As will be described below in more detail, the component RF pulses may be temporally shifted in any number of different combinations while still enjoying the benefits of the present invention. In addition, the component RF pulses may also be assigned different phase values to further reduce peak voltage and/or peak power per pulse. Furthermore, the component RF pulses may be applied with different amplitude modulation functions that are appropriate for the slice location to be imaged, or may be applied with different bandwidths, which result in different slice thickness if appropriate for the targeted studies. These variations in the amplitude modulation function and/or bandwidth can be used to reduce the overall power deposition, or SAR, of the aggregate multiband RF pulse.

Figure 3A:
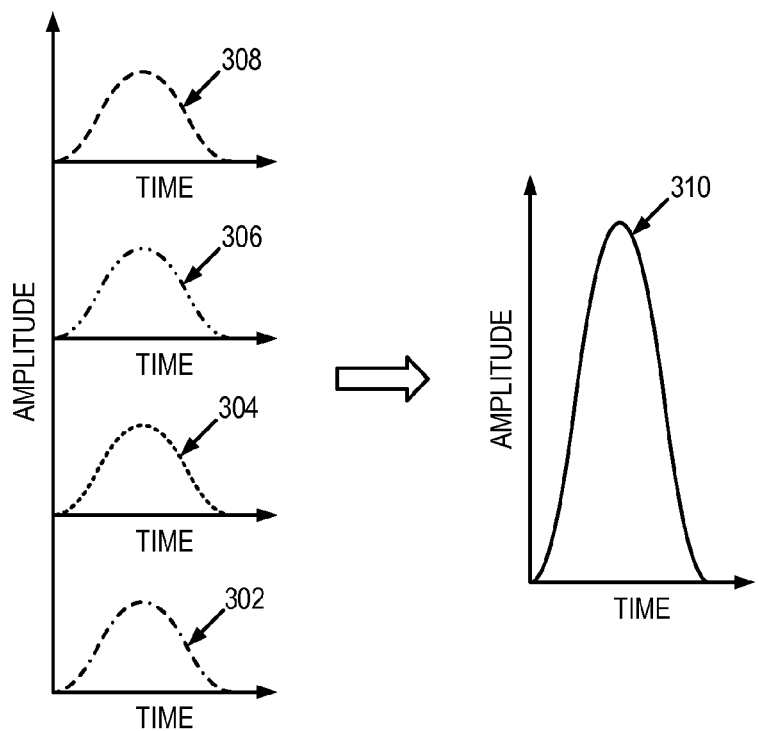
FIG. 3A is an illustration of an example of the amplitude modulation function of a conventional multiband RF pulse having an MB factor of four and its four component RF pulses.

Referring now to FIG. 3A, the conventional approach for designing an example multiband RF pulse having an MB factor of four is illustrated. In the conventional approach, four component RF pulses 302, 304, 306, and 308 are designed to affect the spins in each of four different slices. For example, the frequency content of each of the component RF pulses 302, 304, 306, and 308 is selected to match the Larmor frequency of a spin species as it is modified in each of four desired slice locations by a slice-selection gradient to be applied during an imaging study. The cumulative effect of generating these component RF pulses 302, 304, 306, and 308 at the same time is to generate a multiband RF pulse 310 with an amplitude approximately equal to the sum of the amplitudes of the component RF pulses 302, 304, 306, and 308. Because the component RF pulses 302, 304, 306, and 308 share the same temporal footprint, the increased power required by the multiband RF pulse 310 is deposited to the RF coil and the subject during this same duration of time. It is noted that the pulse shapes depicted in FIG. 3A and elsewhere are for illustration purposes only. The RF pulses can be a sinc pulse or a gauss pulse, both of which are commonly employed pulses in the field; but, the RF pulses can also be shaped using amplitude and frequency modulated pulses (e.g., hyperbolic secant or hyperbolic tangent pulses). It is noted that, for clarity's sake, the RF pulses illustrated herein do not include the high-frequency oscillations that would be present as a result of the component RF pulses being at different frequencies.

Figure 3B:
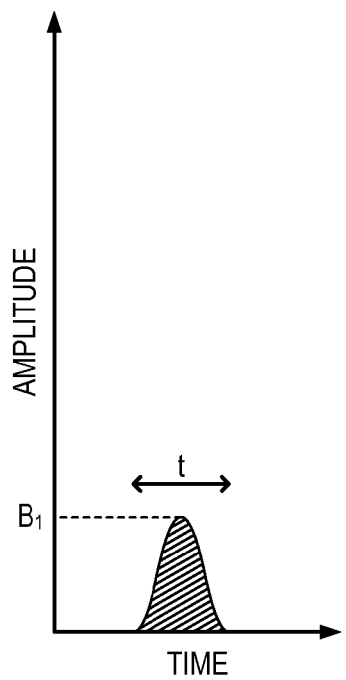
FIG. 3B is an illustration of an example of the amplitude modulation function of a conventional single-band RF pulse.

By way of example, a comparison between a conventional single-band RF pulse, a conventional multiband RF pulse, a stretched multiband RF pulse, and a time-shifted multiband RF pulse is now provided with reference to FIGS. 3B-3E. Beginning with a single-banded Gaussian pulse of duration $t_s$, bandwidth BW, and peak RF field requirement $B_1$, as illustrated in FIG. 3B, conventional N-banded pulses are formed by summing N frequency-shifted copies of the single-banded pulse in the complex domain. Frequency shifts are applied to each band according to the desired slice position of each band, which is determined by the total number of slices in the imaging protocol, the desired overall spatial coverage of the slices, and the slice acceleration (i.e., the MB factor). The spatial inter-slice distance is typically maximized to optimize coil encoding and allow for the most effective unaliasing performance.

The total duration, t, of the conventional N-banded pulse is the same as the base single-banded pulse: $t=t_s$. The peak RF field requirement of the conventional N-banded pulse is approximately $N \cdot B_1$. The specific frequency and phase offsets of the constituent bands can affect this calculation; it has been demonstrated that they can be optimized for the express purpose of peak voltage and power reduction. Such can be used in conjunction with the technique disclosed herein.

N-banded time-shifted multiband pulses may be created with the addition of temporal shifts between the bands. As the temporal shift, $\Delta S$, is increased from zero to $t_s$, the peak RF field requirement of the N-banded time-shifted multiband pulse decreases from $N \cdot B_1$ and approaches $B_1$ very rapidly, such that a $\Delta S < 0.25 \cdot t_s$ produces an N-banded pulse with a peak RF field of close to $B_1$. The total duration, t, of the N-banded time-shifted multiband pulse increases with the temporal shift factor so that $t = N \cdot \Delta S + t_s$.

Figure 3C:
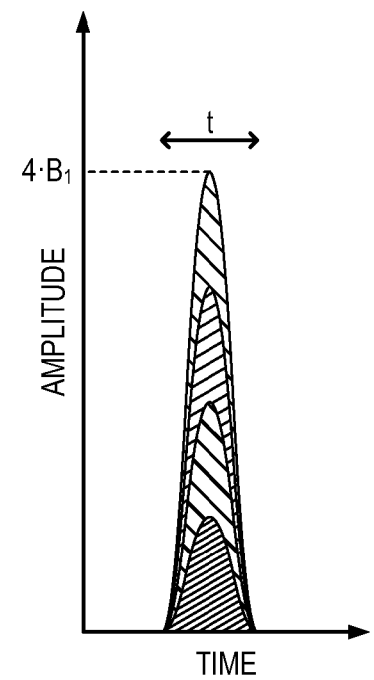
FIG. 3C is an illustration of an example of the amplitude modulation function of a conventional multiband RF pulse having an MB factor of four.
Figure 3D:
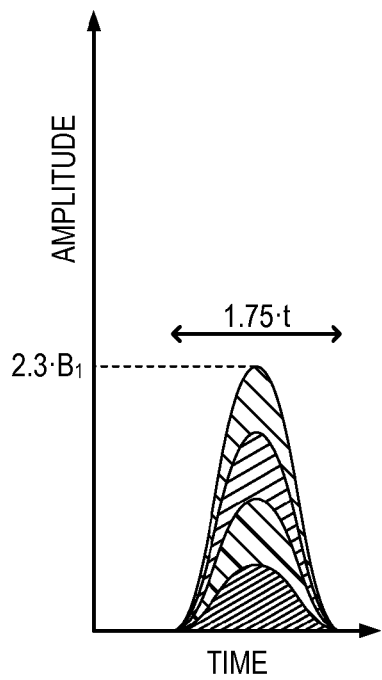
FIG. 3D is an illustration of an example of the amplitude modulation function of the conventional multiband RF pulse of FIG. 3D, which is played out over a longer duration of time so as to decrease its peak power, but also narrow its effective bandwidth.
Figure 3E:
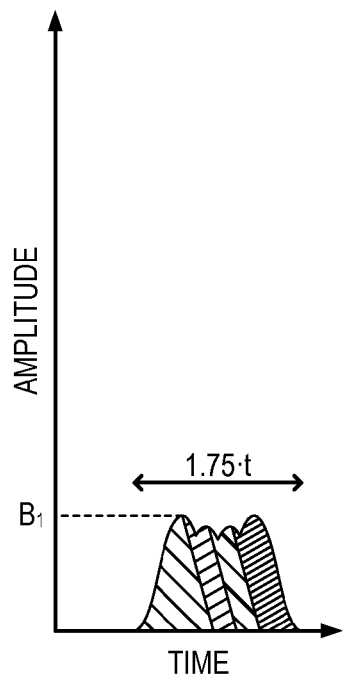
FIG. 3E is an illustration of an example of a time-shifted multiband RF pulse having an MB factor of four and a peak power similar to the single-band RF pulse of FIG. 3B.

A comparison of the real components of four-banded multiband RF pulse generated with the conventional method versus a four-banded multiband RF pulse generated in accordance with the present invention, including a 25 percent temporal shift between the bands, is illustrated in FIGS. 3B-3E. The base single-band RF pulse amplitude modulation function envelope is illustrated in FIG. 3B. The different shaded portions of the multiband RF pulses in FIGS. 3C-3E illustrate the contribution of the individual component RF pulses. When the total duration, t, is held constant between the single-band and conventional MB4 pulses, the effective bandwidth, $BW_{eff}$, also remains constant; however, the peak $B_1$ required for the conventional MB4 pulse is four times that of the base single-band pulse, as illustrated in FIG. 3C. When the conventional MB4 pulse is stretched in duration to $1.75 \cdot t$, as illustrated in FIG. 3D, the peak $B_1$ decreases linearly, but so does the $BW_{eff}$, with deleterious consequences in the pulse profile. The time-shifted MB4 pulse, with the same duration of $1.75 \cdot t$ as the stretched pulse, requires no more peak $B_1$ than the original single-band pulse, as illustrated in FIG. 3E, and also preserves the original effective bandwidth. A discussion of how to design a time-shifted multiband RF pulse is now provided.

Figure 4:
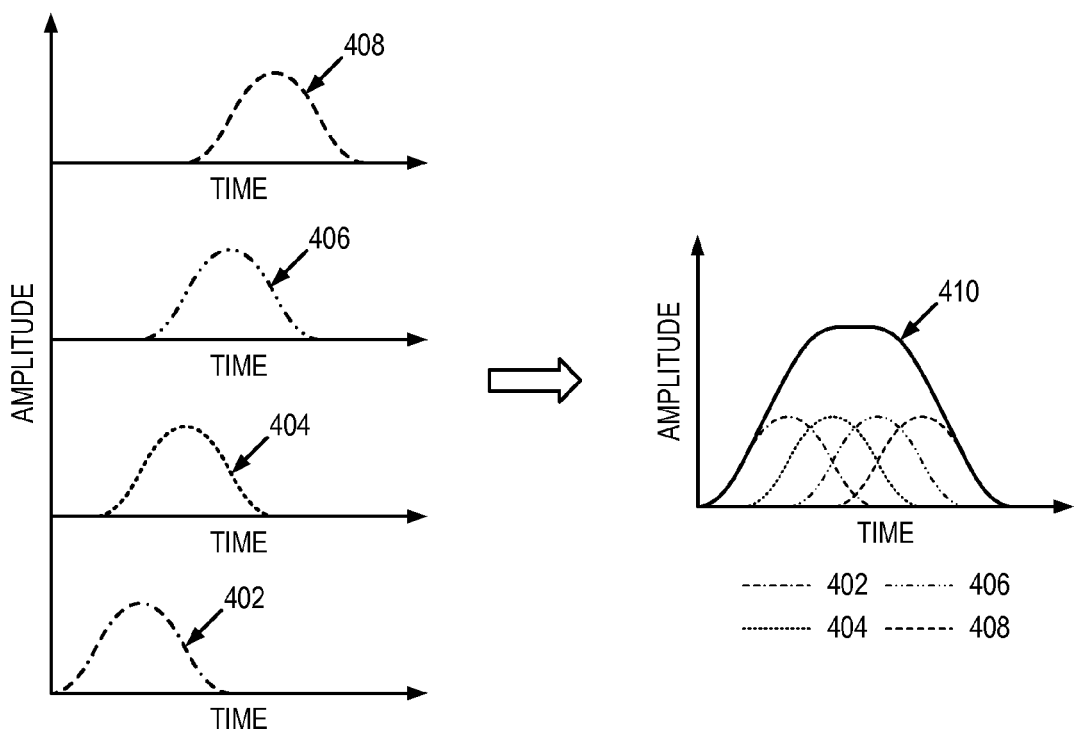
FIG. 4 is an illustration of an example of the amplitude modulation function of a time-shifted multiband RF pulse having an MB factor of four, in which none of the component RF pulses have completely overlapping temporal footprints.

Referring now to FIG. 4, it is an aspect of the present invention to design a multiband RF pulse by temporally shifting the component RF pulses that form a multiband RF pulse relative to each other. By way of example, four component RF pulses 402, 404, 406, and 408 may be generated sequentially. In the example illustrated in FIG. 4, the component RF pulses 402, 404, 406, and 408 are shifted in time such that there is some overlap between temporally adjacent component RF pulses. In doing so, the temporal footprint of the resultant time-shifted multiband RF pulse 410 is greater than the temporal footprint of each component RF pulse 402, 404, 406, and 408 taken alone, or of a conventional multiband RF pulse composed of the same component RF pulses if not temporally shifted relative to each other. The peak voltage, which is directly proportional to the peak amplitude of the pulse, and the peak power corresponding to this peak voltage, is reduced. The power required for the duration of the pulse and deposited on the coil per pulse (some large fraction of which will be deposited in the subject) is the integral with respect to time of the square of the voltage. Thus, while the duration of the overall pulse is elongated fractionally, the drop in the voltage is larger. As a result, the power per pulse may be reduced. Thus, because not all of the component RF pulses 402, 404, 406, and 408 are generated at the same time, the maximum power required by the multiband RF pulse 410 is decreased.

Each component RF pulses does not need to be temporally shifted relative to every other component RF pulses. Instead, in some applications it might be beneficial to temporally shift subgroups of component RF pulses. For example, an MB4 multiband RF pulse can be converted into a time-shifted multiband RF pulse composed of two time-shifted subgroups of MB2 multiband RF pulses.

Figure 5:
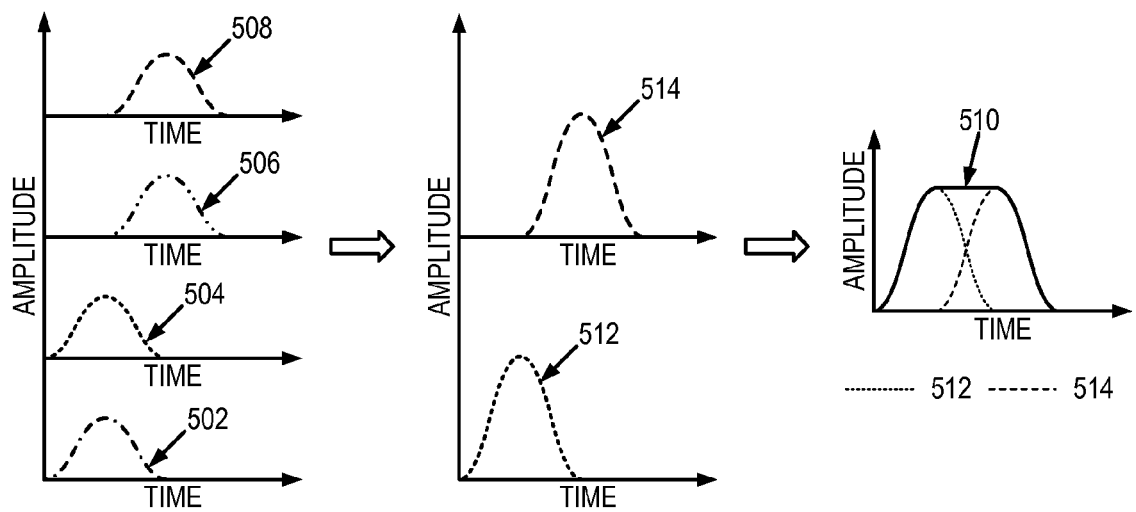
FIG. 5 is an illustration of an example of the amplitude modulation function of a time-shifted multiband RF pulse having an MB factor of four, in which the time-shifted multiband pulse is composed of two multiband RF pulses having MB factors of two and temporal footprints that do not completely overlap.

A generalized example of the foregoing is illustrated in FIG. 5, which illustrated another example of a time-shifted multiband RF pulse in which subgroups of component RF pulses are temporally shifted relative to the others. In this example, rather than temporally shifting each component RF pulse relative to each other, only subgroups of component RF pulses are temporally shifted. Thus, in this example, two component RF pulses 502 and 504 are generated during a first time period and two more component RF pulses 506 and 508 are generated during a second time period. The result of this configuration is the generation of two conventional multiband RF pulses 512 and 514. The first multiband RF pulse is composed of the component RF pulses 502, 504 in the first subgroup of component RF pulses, and the second multiband RF pulse 514 is composed of the component RF pulses 506, 508 in the second subgroup of component RF pulses. Still, the effect of generating two multiband RF pulses 512 and 514 that are temporally shifted relative to each other is the generation of a time-shifted multiband RF pulse 510.

Figure 6:
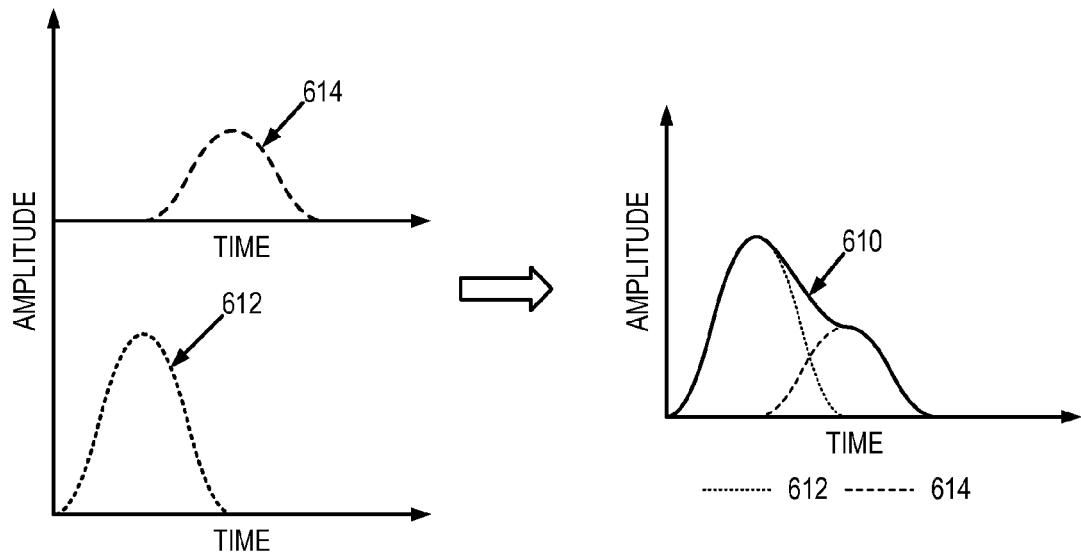
FIG. 6 is an illustration of an example of the amplitude modulation function of a time-shifted multiband RF pulse having an odd-numbered MB factor, in which the time-shifted multiband RF pulse is composed of a component RF pulse with an even-numbered MB factor and a component RF pulse with an odd-numbered MB factor, the component RF pulses having temporal footprints that do not completely overlap.

A time-shifted multiband RF pulse may also be designed such that it is composed of subgroups having unequal MB factors. For example, an time-shifted MB4 multiband RF pulse can be composed of a temporally-shifted MB3 multiband RF pulse and an MB1 (single-band) RF pulse. Such a configuration is not necessarily optimal for even-numbered MB factors; however, this configuration may be beneficial for odd-numbered MB factors. For example, an MB7 multiband RF pulse can be subdivided into temporally-shifted MB3-MB3-MB1 pulses, temporally-shifted MB2-MB2-MB3 pulses, temporally-shifted MB5-MB2 pulses, and so on. One example of such a configuration is illustrated in FIG. 6, which illustrates a time-shifted MB3 multiband RF pulse 610 formed by temporally shifting an MB2 multiband RF pulse 612 and a single-band RF pulse 614.

Figure 7:
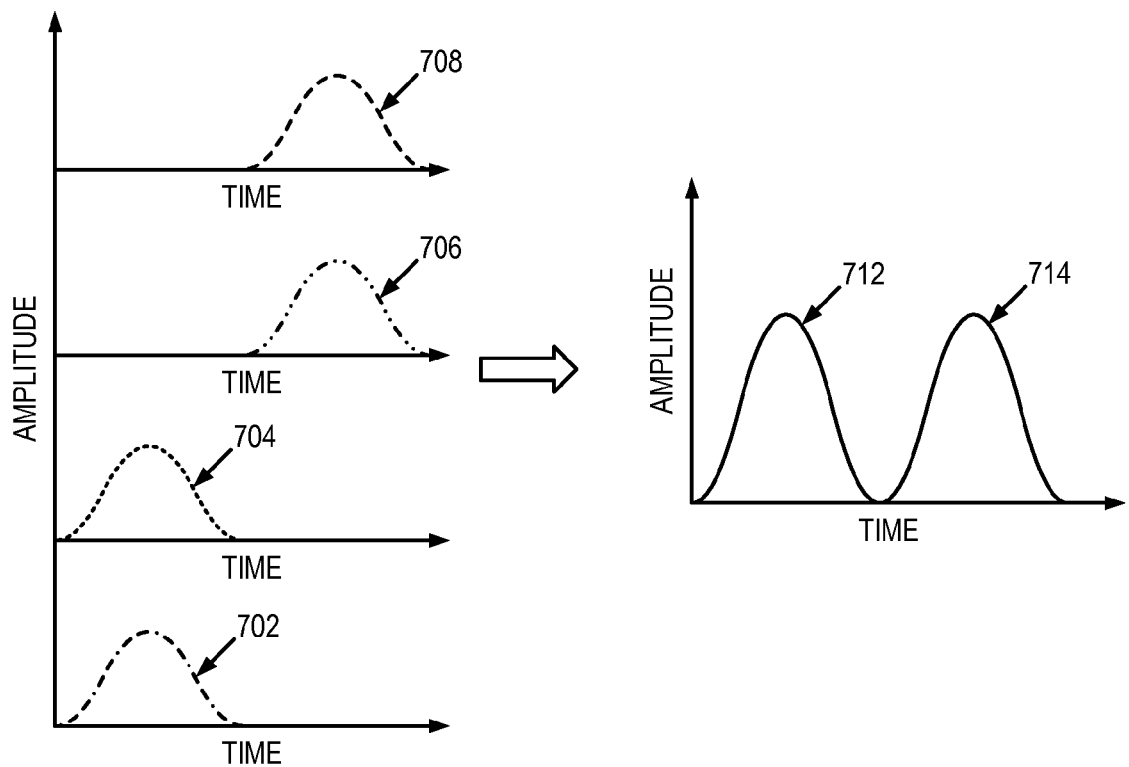
FIG. 7 is an illustration of an example of the amplitude modulation function of a time-shifted multiband RF pulse having an MB factor of four, the time-shifted multiband RF pulse being composed of two subgroups of two component RF pulses in which the temporal footprints of the component pulses within the subgroups are completely overlapping, but the temporal footprints of the two subgroups themselves do not overlap.
Figure 8:
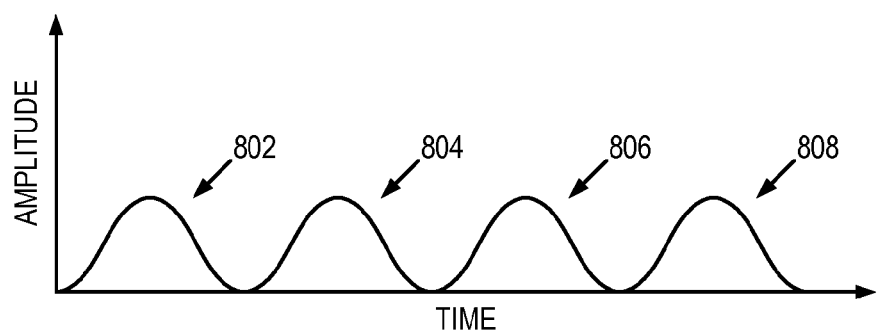
FIG. 8 is an illustration of an example of the amplitude modulation function of a time-shifted multiband RF pulse having an MB factor of four, in which the time-shifted multiband RF pulse is composed of four component RF pulses having temporal footprints that do not overlap at all.

Component RF pulses, or subgroups thereof, can also be partially or fully separated in time, as illustrated in FIGS. 7 and 8. In the example illustrated in FIG. 7, the subgroups of component RF pulses are spaced apart in time such that there is no temporal overlap between the subgroups. Thus, the component RF pulses 702, 704 generated in the first time period to not temporally overlap with the component RF pulses 706, 708 generated in the second time period. In doing so, the multiband RF pulses 712, 714 composed of the subgroups of component RF pulses do not overlap in time. Similarly, in the example illustrated in FIG. 8, the component RF pulses 802, 804, 806, and 808 can be spaced apart in time such that there is no temporal overlap among any of the component RF pulses 802, 804, 806, and 808.

Thus, it will be appreciated by those skilled in the art that time-shifted multiband RF pulses may be generally designed as follows. Each time-shifted multiband RF pulse may be composed of a plurality of component RF pulses, such that at least two of the component RF pulses have different temporal footprints. The time-shifted multiband RF pulse may be composed of temporally-shifted component RF pulses, temporally-shifted subgroups of component RF pulses, or combinations thereof. Moreover, although the examples illustrated in FIGS. 4-8 show uniform time shifts, the component RF pulses, or subgroups thereof, may also be non-uniformly shifted in time relative to each other. Additionally, the amplitude of each component RF pulse can be adjusted relative to the others such that the time-shifted multiband pulse is composed of component RF pulses with different amplitudes. Thus, although it may be preferable to keep the pulse shape (i.e., amplitude, phase, and/or frequency modulation), peak amplitude, and duration of each component RF pulse the same, these parameters can be independently changed as well. Indeed, any of these parameters can be adjusted to uniquely tailor the time-shifted multiband RF pulse and its power deposition and other characteristics. This is useful, for instance, when the $B_1$ field is not uniform, in which instance the amplitude and other characteristics of the component RF pulses can be tailored to compensate for the non-uniformity of the $B_1$ field.

As will now be described in detail, time-shifted multiband RF pulses can be employed in any number of different imaging applications and spatial encoding strategies, including echo planar imaging ("EPI"); controlled aliasing in parallel imaging results in higher acceleration ("CAIPIRINHA") imaging techniques, such as blipped CAIPIRINHA EPI; spiral imaging; gradient-recalled echo ("GRE") imaging, including both radial and rectilinear GRE; steady-state free precession ("SSFP") imaging; and so on. In some instances, such as with GRE-based pulse sequences, additional considerations may be made when using time-shifted multiband RF pulses for excitation. Examples of such considerations are provided below. In addition, time-shifted multiband RF pulses can be employed in combinations of RF pulses, can be interleaved with time delays, and be phase-shifted relative to each other for several different purposes.

The time-shifted multiband RF pulses of the present invention can be used for excitation, refocusing, magnetization preparation with inversion saturation, and the like. When time-shifted multiband RF pulses are used, it is important to note that spins in multiple different slice locations will be affected. When signals are detected from these multiple slice locations during a single readout period using a multichannel receive coil array, the resulting k-space lines corresponding to the different slices and/or images are unaliased using spatial information inherent in the receive coil array.

In general, imaging pulse sequences that makes use of slice-by-slice coverage can be adapted to include time-shifted multiband RF pulses for multislice coverage. It is noted, however, that the substitution of a time-shifted multiband RF pulse for a single band RF pulse may prompt additional considerations in the pulse sequence design. For instance, because the RF pulses are typically applied in the presence of magnetic field gradients, signal losses due to phase dispersion along the applied gradient direction will be present. Thus, these phase dispersions should be accounted for to reduce signal losses. Examples of how to deal with these phase dispersions will be presented below. In all of these cases, the time-shifting procedure described here reduces the peak voltage, peak power, and power per pulse needed to generate the RF pulses. In addition, the magnetic resonance signals formed in response to the time-shifted multiband RF pulses can be positioned relative to each other so that they overlap fully or partially, as desired.

By way of example, time-shifted multiband RF pulses may be used for spin excitation at the beginning of a pulse sequence segment. Such an example would be useful for functional magnetic resonance imaging ("fMRI") applications, among others. Time-shifted multiband RF pulses may also be used as part of a contrast-generating pulse sequence segment. For example, one or more time-shifted multiband RF pulses may be applied subsequent to a spin excitation RF pulse (whether it is a time-shifted multiband RF pulse or not) so as to generate a spin echoes or stimulated echoes. Such sequences can be used for spin-echo or stimulated-echo based anatomical contrast, fMRI, or diffusion-weighted imaging where diffusion weighted gradients are employed during the time periods in between the pulses. Further examples of such applications will be described below. Time-shifted multiband RF pulses may also be used for magnetization preparation to impart selective contrast to the acquired images prior to spin excitation. For example, prior to image acquisition, a time-shifted multiband RF pulse may be used as an inversion RF pulse that inverts spin magnetization in the slices affected by the time-shifted multiband RF pulse followed by a delay. As the end of the delay, image acquisition starts with multiband excitation of the same slices that were inverted and can be followed by additional multiband pulse packets involved in spatial encoding, as in a spin-echo sequence. This procedure imparts $T_1$ contrast. Likewise, a more complex time series of pulses with delays between them, with a multitude of these pulses being a time-shifted multiband RF pulse, may be designed for magnetization preparation prior to spin excitation and image acquisition. One example of such a magnetization preparation is to establish $T_2$-weighting that restores the $T_2$-weighted signal along the z-direction. This example includes a time series of pulses with different tip angles. Moreover, the pulses would have time delays between them, and each pulse in the pulse-delay series would be a time-shifted multiband RF pulse composed of a series of component RF pulses such as, $$\alpha-\tau-(\beta-\tau)_N-(-\alpha)$$

where $\alpha$ and $\beta$ are pulses with nominally 90-degree and 180-degree tip angles, respectively; $\tau$ is a delay time; and N is a non-negative integer designating that the ($\beta-\Sigma$) pulse set is repeated N times. It is noted, however, that $\beta$ and $\tau$ can vary appropriately for each repetition of this pulse set.

Figure 9:
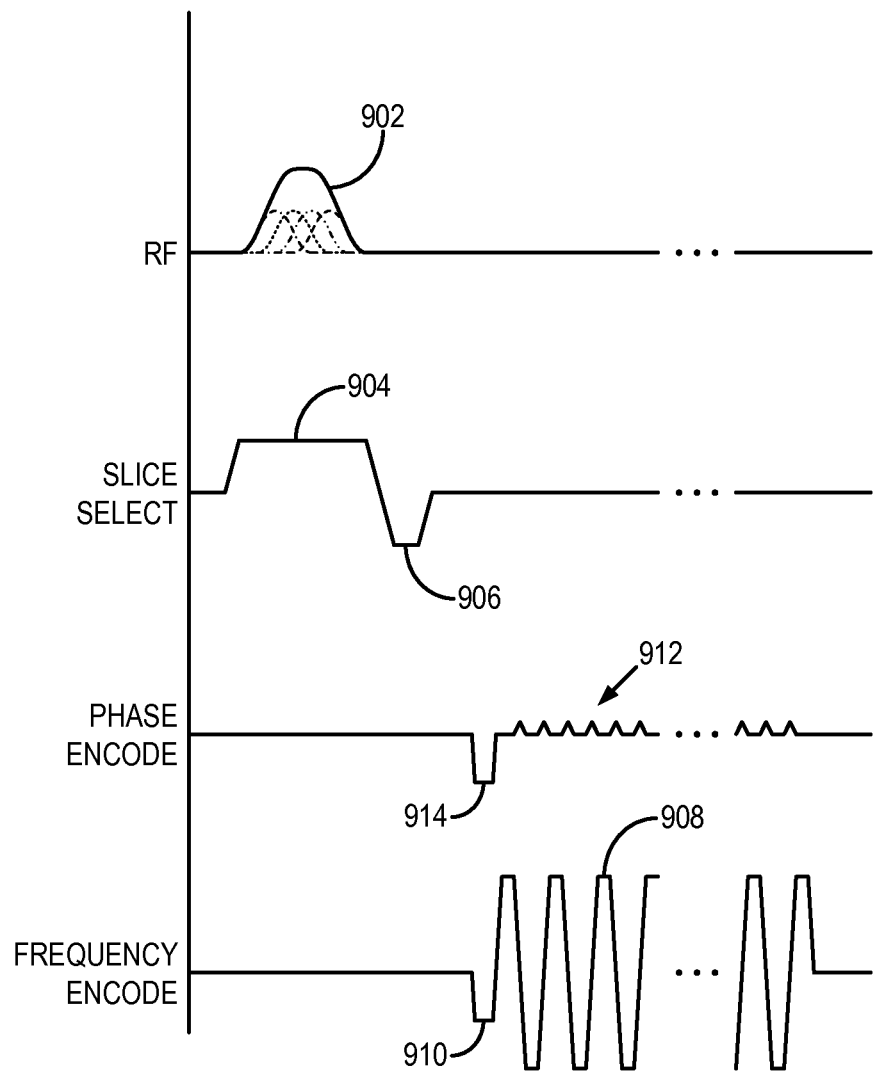
FIG. 9 is an example of a gradient echo pulse sequence that employs a time-shifted multiband RF excitation pulse and an echo planar imaging readout.

Referring now particularly to FIG. 9, an example of a gradient-recalled echo ("GRE") pulse sequence that incorporates time-shifted multiband RF pulses is illustrated. This pulse sequence implements an echo planar imaging ("EPI") spatial-encoding with blipped phase-encoding gradients.

The pulse sequence begins with the application of a time-shifted multiband RF excitation pulse 902, which produces transverse magnetization in multiple slice locations substantially simultaneously. The time-shifted multiband RF excitation pulse 902 is generated in the presence of a slice-selection gradient 904, such that the center frequency of each component RF pulse that forms the time-shifted multiband RF excitation pulse 902 affects spins in the appropriate slice location. The slice-selection gradient 904 concludes with a rephasing gradient lobe 906 that acts to rephase unwanted phase dispersions introduced by the slice-selective gradient 904, such that signal losses resultant from these phase dispersions are mitigated. Additional design considerations related to the rephasing gradient lobe 906 are discussed below.

Following excitation of the spins in the prescribed imaging slices, k-space data is acquired by sampling a series of gradient-recalled echo signals in the presence of an alternating readout gradient 908. The alternating readout gradient is preceded by the application of a pre-winding gradient 910 that acts to move the first sampling point along the frequency-encoding, or readout, direction by a prescribed distance in k-space. Spatial encoding of the echo signals along a phase-encoding direction is performed by a series of phase encoding gradient "blips" 912, which are each played out in between the successive signal readouts such that each echo signal is separately phase-encoded. The phase-encoding gradient blips 912 are preceded by the application of a pre-winding gradient 914 that acts to move the first sampling point along the phase-encoding direction by a prescribed distance in k-space. Together, the pre-winding gradients 910 and 914 act to begin the sampling of k-space at a prescribed k-space location.

When the time-shifted multiband RF excitation pulse 902 is composed of component RF pulses with partially overlapping temporal footprints, the rephasing gradient lobe 906 will not fully rephase the spins excited by each of the component RF pulses. For example, the first component RF pulse of the time-shifted multiband RF pulse will experience a prolonged slice-selection gradient subsequent to its application; thus, the spins excited by this component RF pulse will continue to dephase in the presence of the slice-selection gradient. If the rephasing gradient lobe is designed to correctly rewind the phase dispersions produced by the last component RF pulse, then the rephasing gradient lobe will not be sufficient to rewind the phase dispersions produced by the first component RF pulse. Although this effect is problematic, it can be accounted for using several different approaches.

In one approach, the component RF pulses could be fully separated in time, such as those illustrated in FIG. 8, such that the phase dispersions along the slice direction can be individually corrected. In this approach, the slice-selection gradient 904 is replaced with an alternating waveform, in which the polarity of the gradient is reversed for each subsequent component RF pulse. By using the gradient reversal, the continuous phase accumulation encountered with a constant slice-selection gradient is avoided. At a first glance, this approach may appear similar to the simultaneous image refocusing ("SIR"), also referred to as the simultaneous echo refocusing ("SER"), technique; however, there are significant differences between the two techniques.

In SIR, the echoes from different slice locations are acquired separately in time so as to avoid temporally overlapping these magnetic resonance signals. This is accomplished by applying gradient pulses in the readout direction after each RF excitation pulse, such that when data acquisition proceeds in the presence of a readout gradient, the magnetic resonance signals originating from the different slice locations come into phase and to form an echo at different times. Because the echo signals for the different slices are formed at different times, they can be selectively extracted and subsequently processed. Consequently, the SIR technique does not require an unaliasing procedure; thus, the SIR technique does not make use of multichannel coil sensitivity profiles. The SIR approach of collecting echoes, however, has a major disadvantage: temporally separating the echoes from each slice results in prolonged echo readout trains, which is detrimental to image quality and causes signal loss, image distortions, and blurring.

Contrary to the SIR method, with the technique described above the component RF pulses, which collectively form the time-shifted multiband RF pulse, are fully separated in time, and data is acquired from each slice location simultaneously. Thus, the echo time ("TE") delay for each slice will be slightly different. This acquisition technique does not make use of gradient pulses applied along the readout direction after each RF excitation pulse, as is required with the SIR technique. Alternatively, the echo signals can be partially separated in time, while still overlapping, using some gradient pulses after each component RF pulse is produced; however, unlike SIR this approach would require multichannel coil sensitivity information to unalias the partially overlapped echo signals. Overlapping the echo signals from each slice location partially or fully in time reduces the length of the echo train significantly, thereby avoiding the deleterious consequences of a long readout period.

Another approach for mitigating unwanted phase dispersions resulting from the slice-selection gradient 904 is to use small time shifts between each component RF pulse, such that the differential dephasing is minimal. In this instance, the signal losses resulting from this minimal dephasing can largely be ignored. This approach is particularly feasible when the MB factor is small, such as when the MB factor is around two.

Another approach for mitigating unwanted phase dispersions resulting from the slice-selection gradient 904 is to use component RF pulses that are designed to compensate for the differential phase buildup. For example, each component RF pulse may be designed to impose a predetermined phase pattern along the slice direction in the corresponding slice location. With this approach, each component RF pulse can be encoded with a phase dispersion that compensates for the phase dispersion produced by the slice-selection gradient 904. This approach would require that each component RF pulse in the time-shifted multiband RF pulse have a different pattern.

Figure 10:
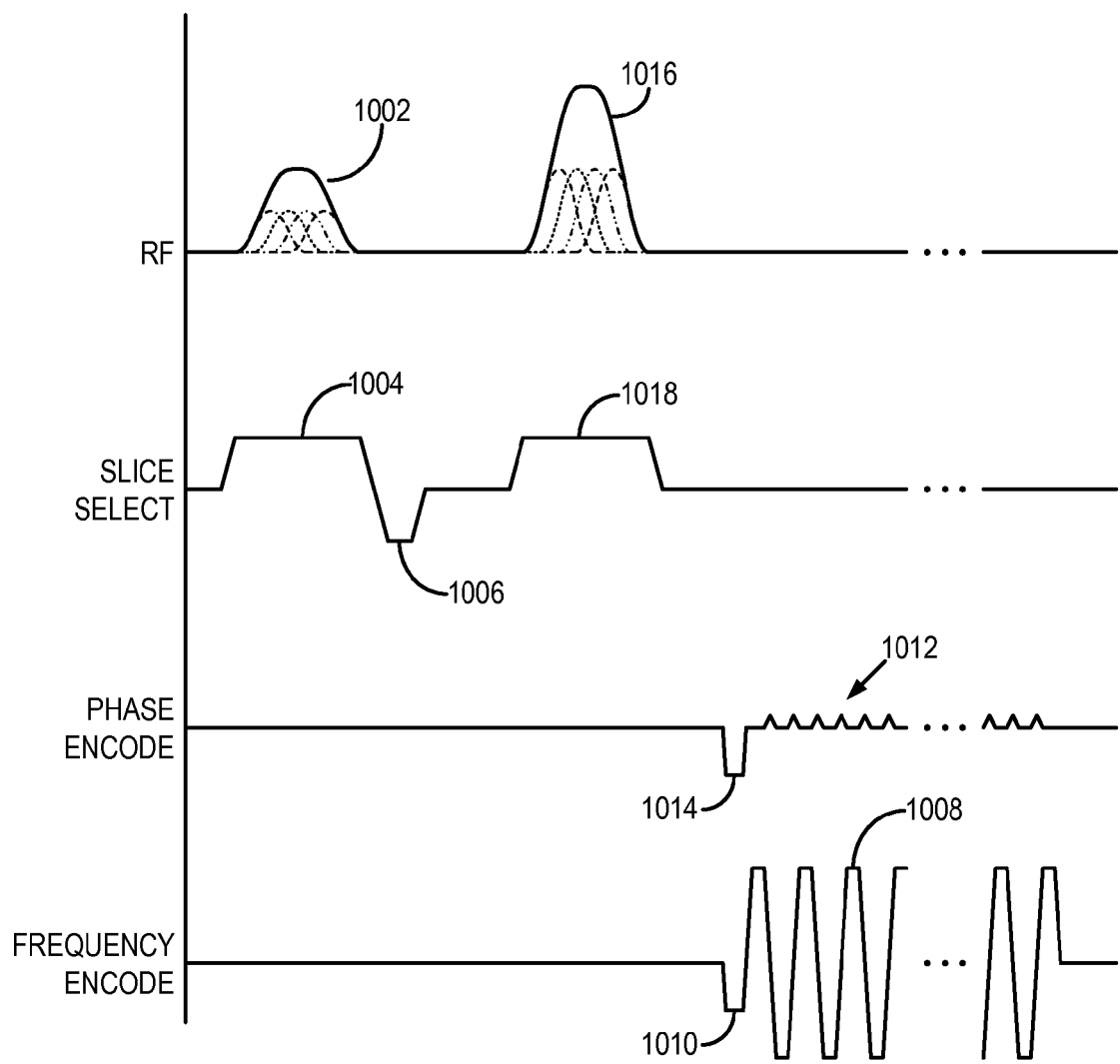
FIG. 10 is an example of a spin-echo pulse sequence that employs a time-shifted multiband RF excitation pulse, a time-shifted multiband RF refocusing pulse, and an echo planar imaging readout.

Referring now to FIG. 10, an example of a spin-echo pulse sequence that incorporates time-shifted multiband RF pulses is illustrated. This pulse sequence implements an EPI spatial-encoding with blipped phase-encoding gradients.

The pulse sequence begins with the application of a time-shifted multiband RF excitation pulse 1002, which produces transverse magnetization in multiple slice locations substantially simultaneously. The time-shifted multiband RF excitation pulse 1002 is generated in the presence of a slice-selection gradient 1004, such that the center frequency of each component RF pulse that forms the time-shifted multiband RF excitation pulse 1002 affects spins in the appropriate slice location. The slice-selection gradient 1004 concludes with a rephasing gradient lobe 1006 that acts to rephase unwanted phase dispersions introduced by the slice-selective gradient 1004, such that signal losses resultant from these phase dispersions are mitigated. Additional design considerations related to the rephasing gradient lobe 1006 are discussed below. Unlike gradient-recalled echo pulse sequences, the differential dephasing that occurs during the application of the slice-selection gradient 1004 that was discussed above can be compensated for in a spin-echo pulse sequence. Example compensations are discussed below in detail.

Next, a time-shifted multiband RF refocusing pulse 1016 is applied in the presence of another slice-selection gradient 1018 so that transverse magnetization produced by the time-shifted multiband RF excitation pulse 1002 is refocused to produce magnetic resonance echo signals.

Following excitation of the spins in the prescribed imaging slices, k-space data is acquired by sampling a series of spin-echo signals in the presence of an alternating readout gradient 1008. The alternating readout gradient is preceded by the application of a pre-winding gradient 1010 that acts to move the first sampling point along the frequency-encoding, or readout, direction by a prescribed distance in k-space. Spatial encoding of the echo signals along a phase-encoding direction is performed by a series of phase encoding gradient "blips" 1012, which are each played out in between the successive signal readouts such that each echo signal is separately phase-encoded. The phase-encoding gradient blips 1012 are preceded by the application of a pre-winding gradient 1014 that acts to move the first sampling point along the phase-encoding direction by a prescribed distance in k-space. Together, the pre-winding gradients 1010 and 1014 act to begin the sampling of k-space at a prescribed k-space location.

Figure 11:
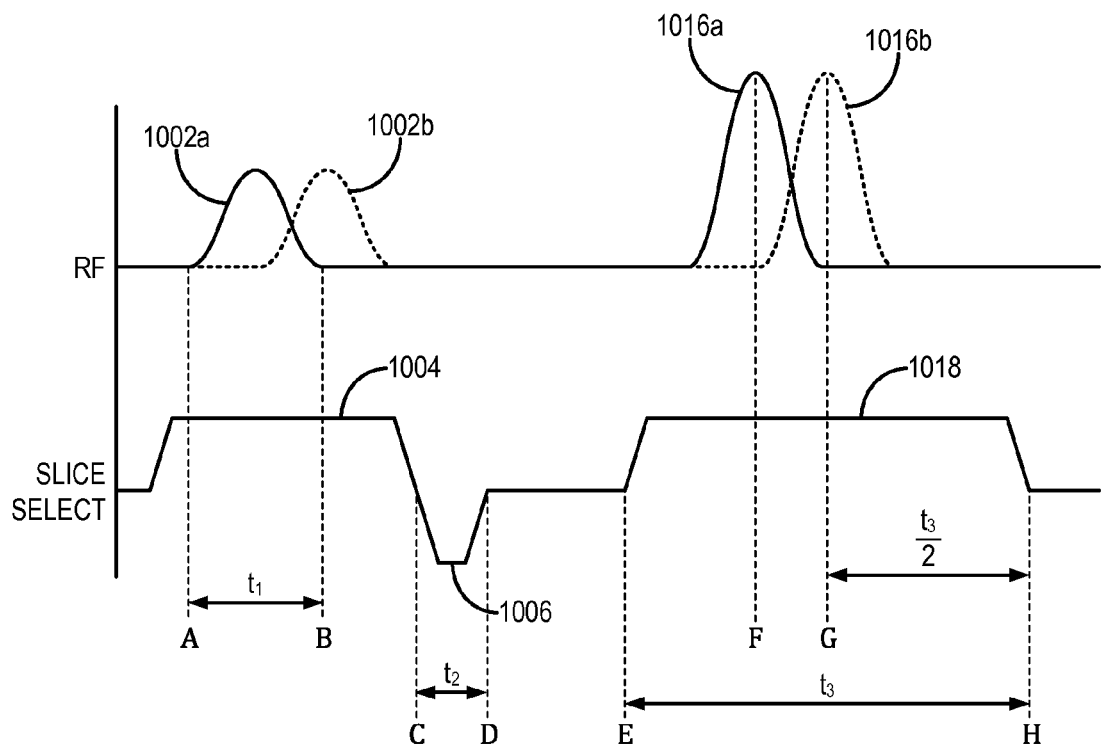
FIG. 11 is an illustration of component RF pulse timings relative to slice-selection gradient timings that mitigate differential dephasing of spins in the different slice locations affected by the different component RF pulses, this example illustrating a single RF excitation and a single RF refocusing.

To compensate for differential phase dispersions generated by the slice-selection gradient 1004 for the different slices excited by the time-shofted composite multiband pulse, the second slice-selection gradient 1018 can be modified. An example of this modification is illustrated in FIG. 11, to which reference is now made. In this example, a time-shifted multiband RF pulse is used for both excitation and refocusing. By way of example, the signal for the slice, or slices, excited by the component RF excitation pulse 1002b can be refocused along the slice-encoding direction at time point D by the reversal of the slice-selection gradient 1004 that is established between time points C and D. The component RF refocusing pulse 1016b for this slice, or these slices, is, in this example, symmetrically positioned in the slice-selection gradient 1018 applied during the refocusing pulse. The duration between time points E and G and between time points G and H must be equal, assuming that the ramp-up and ramp-down of this gradient are also equivalent. More generally, the time integral of the gradient between points E and G is substantially equal to the time integral of the gradient between points G and H. The slice, or slices, excited by the component RF excitation pulse 1002a are not refocused at time point B, C, or D in this configuration. But, the component RF refocusing pulse 1016a for this slice, or these slices, can be positioned so that the time-integral of the slice-selection gradient 1018 from time point F to time point H exceeds that from time point E to time point F so as to compensate for the dephasing induced by the slice-selection gradient 1004 played out during time points A to D in the slice excited by component RF excitation pulse 1002a.

Consider an example in which the rephasing lobe 1006 of the slice-selection gradient 1004 correctly rewinds the phase dispersion caused by the application of the first component RF excitation pulse 1002a and leaves the slice excited by the second component RF excitation pulse 1002b dephased at time point D. In this instance, the first component RF refocusing pulse 1016a must be symmetrically positioned relative to the slice-selection gradient 1018 in the time period between time points E and H, and second component RF refocusing pulse 1016b must be displaced so as to compensate for the residual dephasing and to bring the spins in the corresponding slice location back into phase with each other along the slice direction at time point H. This positioning of the component RF refocusing pulses 1016a, 1016b is the opposite of what is illustrated in FIG. 11.

It is noted that the amplitude of the slice-selection gradients 1004 and 1018 need not be equal. In fact, these gradients 1004, 1018 may even be of opposite polarity. The magnitude of the time-shift between the component RF pulses in the composite multiband excitation and refocusing pulses also need not be the same. This feature can be used to keep the echo time ("TE") the same for all of the different slice locations, or to separate the echo times partially or fully. If the polarity of the slice-selection gradients 1004, 1018 is different, the order of the component RF refocusing pulses will have to be changed. In general, the slice selective and refocusing pulses may be positioned such that phase evolution induced during and subsequent to the slice excitation up to the center of the refocusing pulse by the presence of the gradient patterns and the RF pulse characteristics are cancelled or "rewound" by the phase dispersion that follows due to the time integral of the gradient patterns for the slice-selection gradient and the RF pulse characteristics.

The preceding principles can be extended to time-shifted multiband RF pulses with more than two time-shifted component RF pulses or more than two time-shifted subgroups, each of which is composed of component RF pulses that are not time-shifted relative to each other. For example, when the time-shifted multiband RF excitation pulse 1002 and time-shifted multiband RF refocusing pulse 1016 are composed of two or more components RF pulses, or subgroups of component RF pulses, the phase dispersions can be integrated to zero, or close to zero, using the general principle outlined above.

Note that the echoes formed by the different component RF refocusing pulses may or may not form at the same time. This is immaterial to the subsequent unaliasing that is preformed and may even enhance the unaliasing efficiency when the echoes are shifted relative to each other. The echo time for each echo also may be slightly different, but this difference would be very small compared to the echo time itself.

Although the pulse sequence illustrated in FIG. 10 shows one excitation pulse and one refocusing pulse, it will be appreciated by those skilled in the art that time-shifted multiband RF pulses may be implemented in any number of combinations of excitation and refocusing pulses to generate spin-echoes or stimulated echoes. For example, one or two refocusing pulses with appropriate delays can be used before signal detection. An example of where this configuration of refocusing pulses may be useful is diffusion weighted imaging where the two refocusing pulses may be used to reduce eddy current effects. As before, the refocusing pulses may be designed as having a 180 degree flip angle, but may also be designed to have different flip angles, such as flip angles less than 180 degrees. Another example of a refocusing pulse configuration includes more than two refocusing pulses with interleaved delays, which may be used for Carr-Purcell type weighting.

Figure 12:
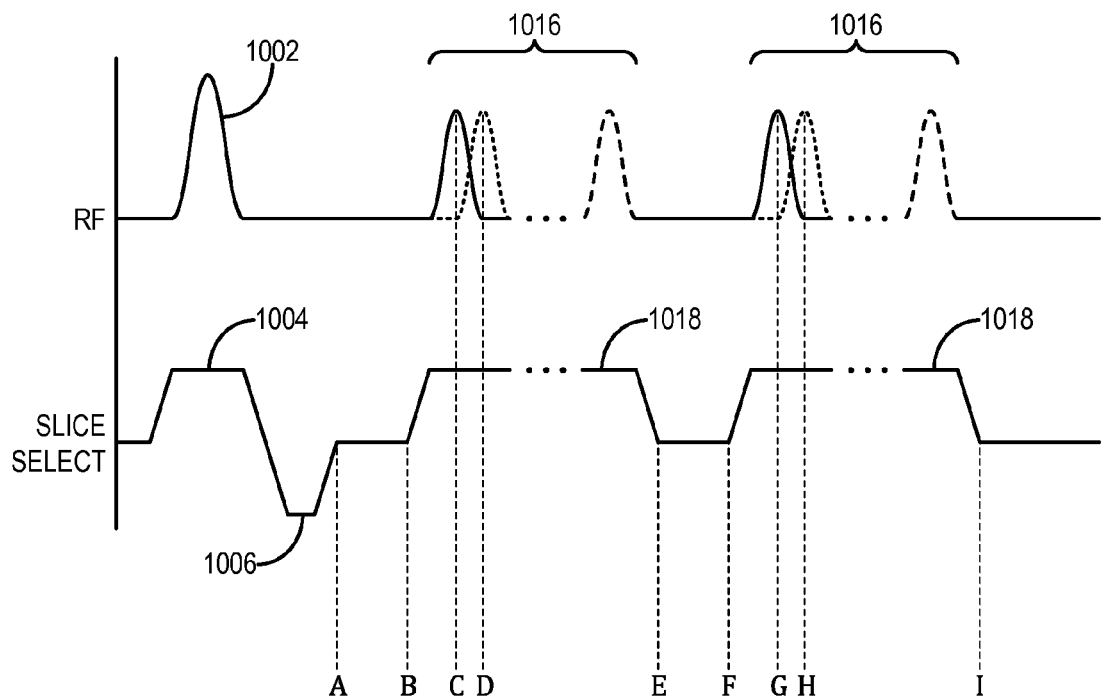
FIG. 12 is an illustration of component RF pulse timings relative to slice-selection gradient timings that mitigate differential dephasing of spins in the different slice locations affected by the different component RF pulses, this example illustrating a single RF excitation and two RF refocusings used for generating spin-echo signals that are subsequently sampled and recorded.

In some imaging applications, such as diffusion weighted magnetic resonance imaging, two refocusing pulses are employed to develop a unique image contrast, to mitigate eddy current effects, or to compensate for RF pulse imperfections. When two such refocusing pulses are single RF pulses or multiband RF pulses without a time-shift, they can be asymmetrically positioned with relative to the slice-selection gradients established during which refocusing pulses are applied. When these two refocusing pulses are time-shifted multiband RF refocusing pulses, their component RF refocusing pulses can be time-shifted using principles described above and asymmetrically placed relative to the slice-selection gradients employed with each refocusing pulse, as illustrated in FIG. 12. In this case, each component RF refocusing pulse in the time-shifted multiband RF refocusing pulse is played out in the same temporal sequence for the two RF refocusing pulses so that it has the same temporal relationship relative to the slice-selection gradient for the refocusing pulses. The dephasing induced by the uneven gradient duration about each component RF refocusing pulse will be cancelled out by the application of the second refocusing pulse and accompanying slice-selection gradient. Also the peak of the echo for signals coming from each slice will be formed at the same time point for each slice.

This pulse sequence design can be extended to pulse sequences that implement more than two refocusing pulses. In these instances, when an even number of refocusing pulses is implemented, the same design considerations as discussed above for the two refocusing pulse case will apply. However, when there is an odd number of refocusing pulses in the pulse sequence, then the two refocusing pulse design considerations should be combined with the one refocusing pulse design considerations discussed above with respect to FIG. 11. It is noted that the slice-selection gradients do not need to be identical as long as the time integral of the relevant portions of the slice-selection gradients are equal, as discussed above.

The preceding examples of using multiple time-shifted multiband RF refocusing pulses describe instances where the refocusing pulses are played out before acquiring spatially-encoded data. However, there are many instances where it is desirable to acquire spatially-encoded data between refocusing pulses. Examples of these instances include using fast spin echo ("FSE") pulse sequences and gradient and spin-echo ("GRASE") pulse sequences, both of which acquire one or more k-space lines between repetitively applied refocusing pulses that follow the excitation. Each of these pulses can be converted into time-shifted multiband RF refocusing pulses to reduce peak power.

Figure 13:
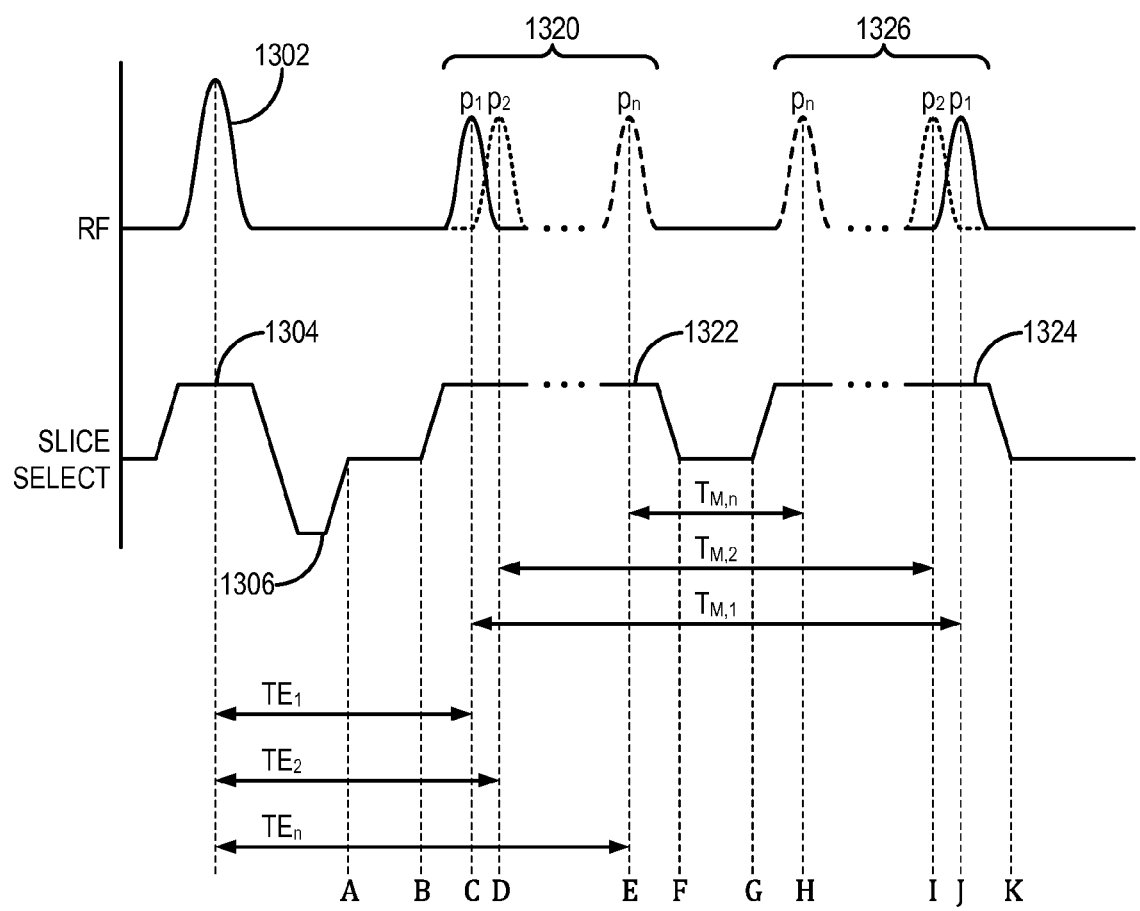
FIG. 13 is an illustration of component RF pulse timings relative to slice-selection gradient timings that mitigate differential dephasing of spins in the different slice locations affected by the different component RF pulses, this example illustrating a stimulated echo imaging.

In addition to the foregoing pulse sequence designs, time-shifted multiband RF pulses can also be used for the formation of stimulated echoes. An example of an excitation pulse configuration useful for generating stimulated echoes includes a first RF pulse followed by a first delay time with a dephasing gradient, a second RF pulse, and then a second delay time. A third RF pulse then leads to a "stimulated" echo using a rephasing gradient that rewinds the phase evolution induced during the first delay period. The first RF pulse provides excitation of the spins and, preferably, the second and third RF pulses have the same flip angle as the first RF pulse, preferably, this flip angle is ninety degrees. In general, stimulated-echo pulse sequences typically include three RF pulses with flip angles around ninety degrees. Each of these RF pulses can be replaced with a time-shifted multiband RF pulse to perform stimulated-echo imaging on multiple slices simultaneously. The principles discussed above for using time-shifted multiband RF refocusing pulses in spin-echo sequences are applicable also to forming stimulated-echoes. However, the temporal order in which component RF pulses are played out is reversed for stimulated-echo sequences. This is illustrated in FIG. 13, in which the order of the component RF pulses $p_1, p_2, \ldots, p_n$ 1320 as they are played out in the presence of slice-selection gradient 1322 is reversed as they are played out in the presence of slice-selection gradient 1324. That is, component pulse, $p_n$, is generated first and component pulse, $p_1$, is generated last. Thus, the gradients are balanced to form the stimulated echo. Using the flat-top trapezoidal gradients as an example as shown in FIG. 13 and again assuming that the spins are in phase at time point A (for illustration purposes), to avoid differential dephasing the time integral of the gradients from time point B to time point C must be the same as from time point J to time point K. Likewise, the time integral from time point B to time point D must be the same as from time point I to time point K, and so on. In this sequence, the stimulated echoes will be formed at the same time point beyond the time point K. Note that in this configuration, each slice will have a slightly different $T_M$ and $TE_n$ period. Note that instead of using the first pulse 1302 as a conventional MB pulse without time-shifting, a time-shifted multiband RF pulse may be used as described above for FIG. 11. In this instance, a spin-echo forms in the period, $T_M$, which can be detected and used. The third pulse group 1326 then must be ordered out so as to balance the gradients as described above for the stimulated echo to form.

Figure 14:
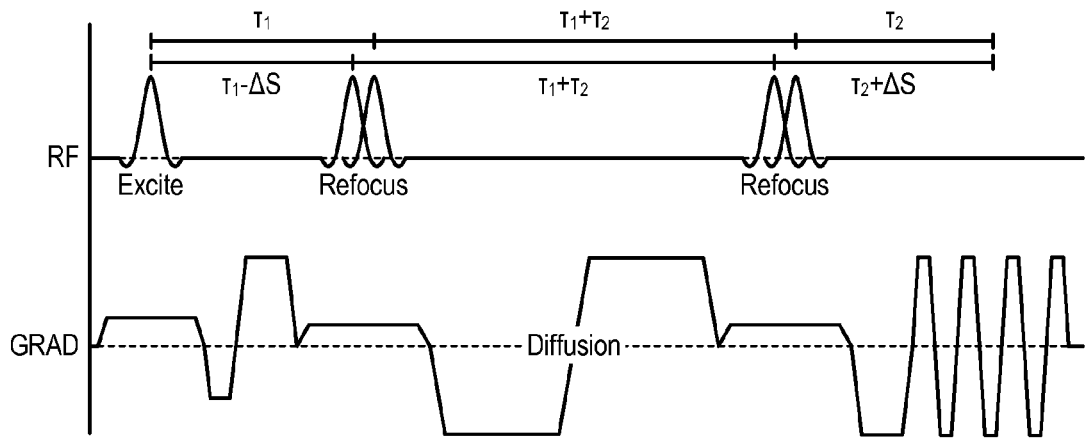
FIG. 14 is an example of a bipolar diffusion-weighted EPI sequence diagram using time-shifted multi-banded refocusing RF pulses, in which no time shift is used for the multi-banded excitation RF pulse.

An example of a diffusion-weighted pulse sequence that implements time-shifted multiband RF pulses is now described. The pulse sequence proposed for bipolar diffusion MRI with time-shifted multiband RF pulses is illustrated in FIG. 14. An two-banded pulse is shown for simplicity. This sequence is based on a standard bipolar diffusion MRI sequence that makes use of an echo-planar imaging ("EPI") readout. Because two refocusing RF pulses are used in this approach, time-shifted multiband refocusing RF pulses can be used in place of single-banded pulses without further modifications to the sequence. The dephasing induced by the asymmetry of the slice-selection gradient moment around the RF of a given band in the first refocusing pulse is balanced by an opposing moment around the second refocusing pulse. In this sequence, no shift is applied to the, nominally ninety degree, multiband RF excitation pulse.

Figure 15:
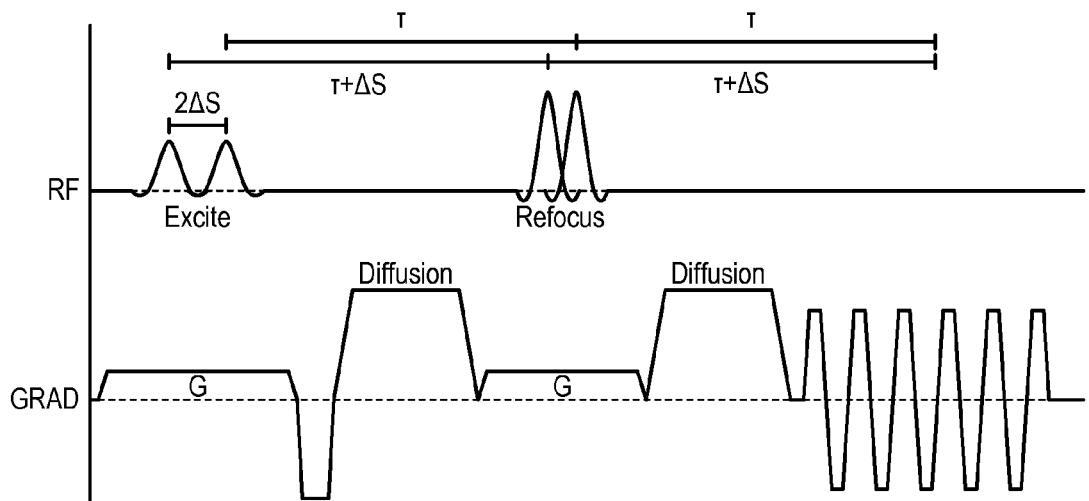
FIG. 15 is an example of an "aligned-echo" monopolar diffusion-weighted EPI sequence using time-shifted multiband refocusing and excitation RF pulses, in which all spin echoes form at the same time, but the effective TE of each band differs by $2 \cdot \Delta S$.
Figure 16:
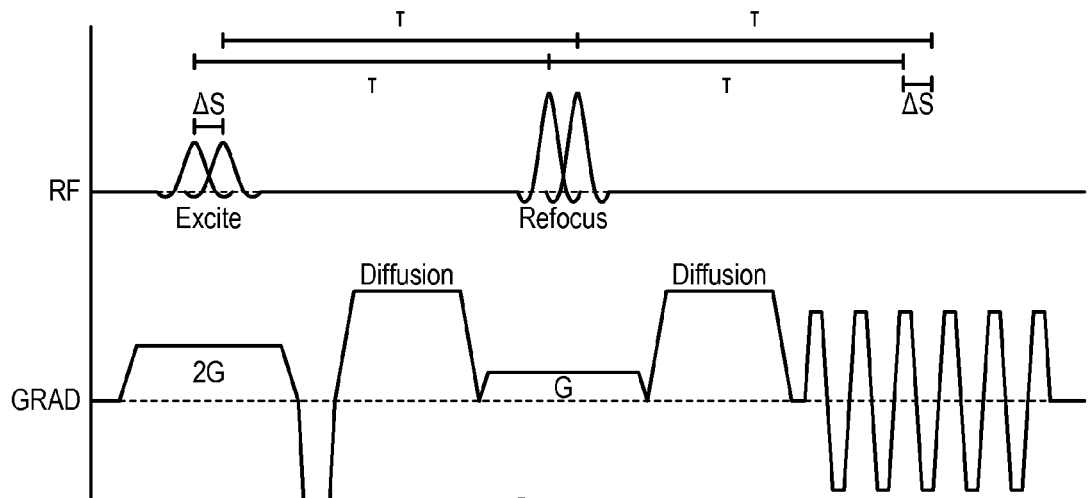
FIG. 16 an example of an "aligned-TE" monopolar diffusion-weighted EPI sequence using time-shifted multiband refocusing and excitation RF pulses, in which the TE of each band is the same, but the formation of the spin echoes for each band is separated in time by $\Delta S$.

Two pulse sequences proposed for monopolar diffusion MRI acquisition with time-shifted multiband RF pulses are presented in FIGS. 15 and 16. The monopolar approach is advantageous primarily because it allows for significantly reduced minimum TE resulting in an SNR gain that is critical in diffusion MRI. The historical drawback of the monopolar sequence is increased sensitivity to eddy currents compared to the bipolar sequence, but recent improvements in gradient coil design and post-processing corrections now allow for it to be used routinely and effectively.

In the monopolar scheme, time shifts are applied to both the refocusing and the excitation pulses in order to balance the slice select gradient moments experienced by each band.

In the first monopolar approach, shown in FIG. 15, single-banded pulses were selected such that the excitation and refocusing pulse bandwidths, and therefore the slice select gradient amplitudes, were equal. In this case, a time shift, $\Delta S$, is used between the component RF pulses of the time-shifted multiband RF excitation pulse that is double that of the refocusing pulse time shift in order for the slice select gradient moments to balance. A consequence of this approach is that the effective TE of each band differs by $2 \cdot \Delta S$. The spin echo for each band is formed at the same time, however. This approach may be referred to as an "aligned-echo" monopolar approach.

In the second monopolar approach, shown in FIG. 16, the RF bandwidth and therefore the slice select gradient amplitude required for excitation is double of that used for refocusing. In this case, the slice select gradient moments balance when the time shifts between bands for excitation and refocusing are equal. It then follows that the same TE is realized for all bands. Unlike the approach in FIG. 15, however, the spin echoes are formed at different times for each band, separated by $\Delta S$. This approach may be referred to as an "aligned-TE" monopolar approach.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing images depicting each of a plurality of slice locations in a subject using a magnetic resonance imaging (MRI) system, the steps of the method comprising:
   a) directing the MRI system to perform a pulse sequence that includes generating a multiband radio frequency (RF) pulse by generating at least two component RF pulses, each component RF pulse having a center frequency associated with a different slice location and each component RF pulse being generated at a different time;
   b) acquiring with the MRI system, k-space data from the plurality of slice locations by sampling magnetic resonance signals formed in response to the multiband RF pulse generated in step a); and
   c) reconstructing images depicting each of the plurality of slice locations in the subject from the acquired k-space data.

2. The method as recited in claim 1 in which at least one of the component RF pulses is a multiband RF pulse that is configured to manipulate spin magnetization in a plurality of slice locations.

3. The method as recited in claim 2 in which the multiband RF pulse is a time-shifted multiband RF pulse that is composed of at least two component RF pulses having temporal footprints that do not completely overlap.

4. The method as recited in claim 1 in which the different times at which each component RF pulse is generated are selected such that a temporal footprint of each component RF pulse partially overlaps with a temporal footprint of at least one other component RF pulse.

5. The method as recited in claim 1 in which the different times at which each component RF pulse is generated are selected such that each component RF pulse has a temporal footprint that does not overlap with a temporal foot print of another component RF pulse.

6. The method as recited in claim 1 in which step a) includes performing a pulse sequence that also includes generating a multiband RF refocusing pulse by generating at least two component RF refocusing pulses, each component RF refocusing pulse having a different center frequency associated with a different slice location and each component RF refocusing pulse being generated at a different time such that a temporal footprint of each component RF refocusing pulse partially overlaps with a temporal footprint of at least one other component RF refocusing pulse.

7. The method as recited in claim 6 in which step a) includes performing a pulse sequence that also includes establishing a slice-selection gradient as the multiband RF refocusing pulse is generated and asymmetrically positioning the component RF refocusing pulses with respect to the slice-selection gradient such that differential dephasing of spins in the different slice locations is mitigated.

8. The method as recited in claim 6 in which the component RF refocusing pulses are asymmetrically positioned in the temporal footprint of the multiband RF refocusing pulse so as to cancel differential dephasing caused by the multiband RF pulse generated in step a).

9. The method as recited in claim 6 in which the at least two component RF pulses each have a bandwidth that is equal to a bandwidth of each of the at least two component RF refocusing pulses, and in which the at least two component RF refocusing pulses are each separated by a time shift with a duration that is twice a duration of a time shift separating each of the at least two component RF refocusing pulses.

10. The method as recited in claim 6 in which the at least two component RF pulses each have a bandwidth that is twice a bandwidth of each of the at least two component RF refocusing pulses, and in which each of the at least two component RF pulses are separated by a time shift with a duration that is equal to a time shift separating each of the at least two component RF refocusing pulses.

11. The method as recited in claim 1 in which the component RF pulses are designed to impose a different phase pattern along different slice-encoding directions, such that differential dephasing of spins in the different slice locations is mitigated.

12. The method as recited in claim 1 in which each of the component RF pulses have at least one of a different amplitude modulation, a different frequency modulation, a different peak amplitude, and a different duration.

13. The method as recited in claim 1 in which each of the at least two component RF pulses have a different phase that is shifted relative to the other component RF pulses.

14. A magnetic resonance imaging (MRI) system, comprising:
a magnet system configured to generate a polarizing magnetic field about at least a portion of a subject arranged in the MRI system;
a plurality of gradient coils configured to apply a magnetic gradient field to the polarizing magnetic field;
a radio frequency (RF) system including at least one RF coil configured to apply an RF field to the subject and to receive magnetic resonance signals therefrom;
a computer system programmed to:
direct the RF system to generate a time-shifted multiband RF pulse that rotates spin magnetization in a plurality of slice locations in the subject, the time-shifted multiband RF pulse being composed of at least two component RF pulses, each component RF pulse having a different center frequency associated with a different one of the plurality of slice locations and each component RF pulse having a temporal footprint that partially overlaps a temporal footprint of another component RF pulse;
direct the RF system to receive magnetic resonance signals formed in response to the time-shifted multiband RF pulse, the magnetic resonance signals being received from the plurality of slice locations; and
reconstruct images depicting each of the plurality of slice locations in the subject from the received magnetic resonance signals.

15. The MRI system as recited in claim 14 in which the computer system is programmed to direct the RF system to generate at least one of the component RF pulses as a multiband RF pulse that is configured to manipulate spin magnetization in a plurality of slice locations.

16. The MRI system as recited in claim 14 in which the multiband RF pulse is a time-shifted multiband RF pulse that is composed of at least two component RF pulses having temporal footprints that do not completely overlap.

17. The MRI system as recited in claim 14 in which the computer system is programmed to direct the RF system to generate the time-shifted multiband RF pulse such that the temporal footprint of each component RF pulse does not overlap the temporal footprint of another of the component RF pulses.

18. The MRI system as recited in claim 14 in which the computer system is programmed to generate a time-shifted multiband RF refocusing pulse that is composed of at least two component RF refocusing pulses, each component RF refocusing pulse having a different center frequency associated with a different one of the plurality of slice locations and each component RF refocusing pulse being generated at a different time such that each of the component RF refocusing pulses do not have completely overlapping temporal footprints.

19. The MRI system as recited in claim 18 in which the computer system is programmed to:
direct the plurality of gradient coils to establish a slice-selection gradient as the time-shifted multiband RF refocusing pulse is generated; and
direct the RF system to asymmetrically position the component RF refocusing pulses with respect to the slice-selection gradient such that differential dephasing of spins in the different slice locations is mitigated.

20. The MRI system as recited in claim 14 in which the computer system is programmed to direct the RF system to generate the component RF pulses such that each component RF pulse imposes a different phase pattern along a slice-encoding direction, such that differential dephasing of spins in the different slice locations is mitigated.

21. The MRI system as recited in claim 14 in which the computer system is programmed to direct the RF system to generate each of the component RF pulses with at least one of a different amplitude modulation, a different frequency modulation, a different peak amplitude, and a different duration.

22. A method for producing images, each of which depict a different one of a plurality of slice locations in a subject, using a magnetic resonance imaging (MRI) system, the steps of the method comprising:
a) directing the MRI system to perform a pulse sequence that includes generating a multiband radio frequency (RF) pulse by generating at least:
i) a first component RF pulse having a center frequency associated with a first slice location, the first component RF pulse being generated at a first time;
ii) a second component RF pulse having a center frequency associated with a second slice location that is different than the first slice location, the second component RF pulse being generated at a second time that is shifted relative to the first time;
b) acquiring with the MRI system, k-space data from the plurality of slice locations by sampling magnetic resonance signals formed in response to the multiband RF pulse generated in step a); and
c) reconstructing images depicting each of the plurality of slice locations in the subject from the acquired k-space data.

23. The method as recited in claim 22 in which step a) includes performing a pulse sequence to form a stimulated echo by generating at least three multiband RF pulses, each multiband RF pulse being generated by generating at least:
i) a first component RF pulse having a center frequency associated with a first slice location, the first component RF pulse being generated at a first time; and ii) a second component RF pulse having a center frequency associated with a second slice location that is different than the first slice location, the second component RF pulse being generated at a second time that is shifted relative to the first time.

24. The method as recited in claim 22 in which step a) includes performing a pulse sequence to form at least one echo by generating at least three multiband RF pulses, each multiband RF pulse being generated by generating at least:
  i) a first component RF pulse having a center frequency associated with a first slice location, the first component RF pulse being generated at a first time;
  ii) a second component RF pulse having a center frequency associated with a second slice location that is different than the first slice location, the second component RF pulse being generated at a second time that is shifted relative to the first time; and
  wherein the component RF pulses are asymmetrically positioned relative to a slice-selection gradient so as to mitigate differential dephasing of spins in the different slice locations.

* * * * *